United States Patent [19]

McKinney

[11] Patent Number: 5,302,756
[45] Date of Patent: Apr. 12, 1994

[54] AMMONOLYSIS OF NYLON

[75] Inventor: Ronald J. McKinney, Wilmington, Del.

[73] Assignee: E. I. Du Pont de Nemours and Company, Wilmington, Del.

[21] Appl. No.: 997,612

[22] Filed: Dec. 23, 1992

[51] Int. Cl.⁵ .................. C07C 209/62; C08J 11/04
[52] U.S. Cl. .................................. 564/488; 521/49.8; 540/485; 540/538; 540/540; 558/311; 558/313; 558/318; 558/445; 558/452; 558/454; 558/456; 562/590; 562/593; 564/198; 564/498; 564/511
[58] Field of Search ............... 521/49.8; 564/511, 488, 564/498, 198; 562/590, 593; 540/485, 538, 540; 558/311, 313, 318, 445, 454, 456, 452

[56] References Cited

U.S. PATENT DOCUMENTS

| | | |
|---|---|---|
| 2,343,174 | 2/1944 | Edison et al. |
| 3,812,055 | 5/1965 | Bonfield et al. |
| 4,085,130 | 4/1978 | Cobb ............................ 260/465.2 |
| 4,720,328 | 1/1988 | Corbin et al. ...................... 540/540 |
| 4,973,746 | 11/1990 | Blackmon et al. ................ 562/442 |

FOREIGN PATENT DOCUMENTS

| | | |
|---|---|---|
| 715592 | 8/1965 | Canada . |
| 739505 | 7/1966 | Canada . |
| 53-28893 | 8/1978 | Japan . |
| 54-84525 | 7/1979 | Japan . |
| 1172997 | 12/1969 | United Kingdom . |

OTHER PUBLICATIONS

Chem. Abs., vol. 94, 32349c (1981).
Golubev et al., Chem. Abs., vol. 107, 79291e (1987).
Ohtsubo et al., Chem. Abs., vol. 81, 78426k (1974).

Primary Examiner—Glennon H. Hollrah
Assistant Examiner—S. Rand

[57] ABSTRACT

Useful monomeric products are obtained in the reaction of nylon 6,6 with ammonia. Increased yield of monomer products from nylon 6,6 is obtained from ammonolysis when a mixture with nylon 6 is employed.

10 Claims, No Drawings

AMMONOLYSIS OF NYLON

BACKGROUND OF THE INVENTION

Japanese Patent Application Publication 54-84,525 (1979) describes a process for the production or 6-aminocapronitrile (6ACN) and caprolactam (CL) by treating molten polycaproamide (nylon 6) at elevated temperature (340° C.) and pressure (6 kg/cm$^2$) with ammonia gas. British Patent 1,172,997 discloses conversion of a polyamide into monomeric compounds by heating the polyamide with ammonia in the presence of hydrogen and a hydrogenation catalyst. The patent exemplifies the process with polyhexamethylene adipamide (nylon 6,6) and with nylon 6. With nylon 6,6, the products are hexamethylene diamine (HMD) and hexamethyleneimine and a small amount of unidentified material. When using nylon 6 in accordance with the patented process, one is said to obtain HMD, hexamethyleneimine and N-(6-aminohexyl)-hexamethyleneimine. It is an object of the present invention to obtain a mix of monomers from nylon 6,6 or a mixture of nylon 6,6 and nylon 6 which can be used for reconversion into useful polyamides or for other purposes.

SUMMARY OF THE INVENTION

The present invention provides a process for preparing a mixture of monomers suitable for conversion to HMD by reacting nylon 6,6 or a mixture of nylon 6,6 and nylon 6, with at least 1 equivalent of ammonia per amide group of the polymer at a temperature between 250 and 400° C. and at a pressure of at least 100 psig, the ratio of nylon 6,6 to nylon 6 in said mixture being from 1:9 to 9:1 on a weight basis.

DETAILED DESCRIPTION OF THE INVENTION

In accordance with the present invention, it has been discovered that a plurality of useful monomers may be prepared from nylon 6,6. The monomers may be separately recovered if desired, but more preferably may be converted to HMD by various treatments. Furthermore, it has been discovered that greatly improved yields of desirable monomers are obtained from nylon 6,6 when an amount of nylon 6 is added to nylon 6,6 ranging from about 1:9 to 9:1, preferably from about 1:2 to 2:1, weight basis, and subjected to the process of this invention. The general procedure involves heating the nylon mixture with ammonia at elevated temperature and pressure. Sufficient ammonia is employed to provide at least 1 mole of ammonia per mole of amide groups in the nylon polymer. Preferably an excess of ammonia is employed. The reaction proceeds at temperatures between 250° to 400° C. It is preferred to use temperatures of from 300° to 350.C for efficient operation. The reaction rate is also pressure dependent with pressures of 100 to 5000 psig being preferred and 500 to 2500 psig being most preferred. The procedure can be performed as a batch or continuous process, the latter being much preferred. The monomer products generally include HMD, 5-cyanovaleramide (CVAM), adiponitrile (ADN), CL, 6-aminocaproamide (ACAM), and 6ACN. The identification of the monomers and the content of each monomer in the recovered monomer mixture can be determined by quantitative gas-liquid chromatography.

The reaction co-produces water which, because of the equilibrium nature of the reaction, inhibits complete conversion of the intermediately formed amides to nitriles. To further the conversion to nitriles, it is desirable to remove the water as it is formed, thereby shifting the equilibrium. This may be accomplished by passing ammonia through the reaction zone and out through a pressure letdown device, such as a backpressure regulator. In this manner, monomer products may also be removed from the reactor as they are formed and collected. Ammonia is not condensed with the monomers and passes into a subsequent chamber. An inert carrier such as nitrogen gas may be substituted for some of the excess ammonia. The monomeric products may then be hydrogenated to HMD. Those monomers which are not converted to HMD may be recycled through the process.

Whereas the reaction proceeds as described above in the absence of catalyst, rates of conversion increase in the presence of a phosphate catalyst such as phosphoric acid, an ammonium phosphate or BPO$_4$.

The following examples are illustrative of the invention and are not intended as limiting.

EXAMPLE 1

A vertical cylindrical reactor (72 cc inner volume) with a 5 micron fritted disk at the bottom is charged with nylon 6,6 (15.0 g.), and (NH$_4$)$_2$HPO$_4$, 0.25 g), sealed and purged with nitrogen. Liquid ammonia is fed (2.0 cc/min) into the reactor through a preheater (320° C.) and the fritted disk. The reactor is heated by means of a band heater of 320° C. Constant pressure in the reactor is maintained by means of Grove back pressure regulator at 1000 psig throughout the reaction period (90 minutes). Monomeric products are volatilized under reaction conditions and carried from the reactor, through the Grove regulator and condensed out of the ammonia stream in a cool receiver. The ammonia passes out of the receiver into a water scrubber. The monomeric products in the receiver are analyzed by quantitative gas-liquid chromatography. Product yields (mole percent based on nylon 6,6 charged) are: HMD, 18%; ADN, 17%; CVAM, 2%.

EXAMPLE 2

In a manner similar to Example 1, a mixture of nylon 6,6 (7.5 g) and nylon 6 (7.5 g) and ammonium phosphate (0.25 g), is reacted with ammonia for 90 minutes. Product yields (mole percent) based on nylon 6,6 charged are: HMD, 56%; ADN, 38%; CVAM, 3%; and based on nylon 6 charged are: 6ACN, 50%; CL, 37%; ACAM, 1%.

EXAMPLE 3

This example illustrates the improved overall conversion of nylon to useful monomeric products when mixtures of nylon 6,6 and nylon 6 are used instead of pure nylon 6,6 alone.

In a manner similar to Example 2, mixtures of nylon 6,6 and nylon 6, in proportions described in Table 1, were reacted with ammonia for 90 minutes. The results are compared with those of Examples 1 and 2.

TABLE 1

| | Effect of nylon 6 on nylon 6,6 yield | | |
|---|---|---|---|
| | Ratio | Monomeric Products from | | Overall Yield to |
| Item | 66:6 Nylon | 66 | 6 | Monomeric Products |
| 1 (Ex. 1) | 100:0 | 18% | — | 18% |
| 2 | 90:10 | 25% | 61% | 29% |

TABLE 1-continued

Effect of nylon 6 on nylon 6,6 yield

| Item | Ratio 66:6 Nylon | Monomeric Products from 66 | Monomeric Products from 6 | Overall Yield to Monomeric Products |
|---|---|---|---|---|
| 3 | 80:20 | 38% | 66% | 43% |
| 4 | 67:33 | 38% | 73% | 50% |
| 5 (Ex. 2) | 50:50 | 48% | 88% | 68% |
| 6 | 33:67 | 44% | 88% | 73% |

Where product yields are calculated as follows:

Monomeric products from 6 =
100 × [(CL)+(6ACN)+(ACAM]/(nylon 6)

Monomeric products from 66 =
100 × [(ADN)+(CVAM)+(HMD)]/2(nylon 6,6)

Overall yield to monomeric products =

{[% 6 monomers × (6 nylon)] + [% 66 monomers ×

(nylon 6,6)}/[(nylon 6) + (nylon 6,6)]

where the values in parentheses are the moles of product or the equivalents of nylon polymer
(eq. wt. for nylon 6 = 113;
eq. wt. for nylon 6,6 = 226).

EXAMPLE 4

This example illustrates the effects of reaction temperature.

In a manner similar to Example 2, except without ammonium phosphate catalyst, a 1:1 mixture of nylons 6,6 and 6 were reacted with ammonia at different temperatures for 90 minutes. The results are shown in Table 2.

TABLE 2

Temperature Effects

| Item | Temperature (°C.) | Monomeric Products from 66 | Monomeric Products from 6 | Overall Yield to Monomeric Products |
|---|---|---|---|---|
| 7 | 300 | 27% | 48% | 38% |
| 8 | 320 | 31% | 56% | 44% |
| 9 | 330 | 40% | 68% | 54% |
| 10 | 340 | 43% | 88% | 65% |

EXAMPLE 5

This example illustrates the effects of reaction pressure and ammonia flow rate. As the pressure is increased, the density of the ammonia in the reactor increases and the ammonia feed must be increased in order to sweep the reactor vapor space at the same rate. Accordingly, the ammonia flow has been adjusted to maintain the same hold up time in the vapor space at each pressure.

In a manner similar to Example 2, a 1:1 mixture of nylon 6,6 and 6 was reacted at 320° C. for 90 minutes at different pressures and ammonia flow rates. The results are shown in Table 3.

TABLE 3

Pressure Effects

| Item | Pressure (psig) | Monomeric Products from 66 | Monomeric Products from 6 | Overall Yield to Monomeric Products |
|---|---|---|---|---|
| 11 | 500 | 30% | 54% | 42% |
| 12 | 1000 | 49% | 88% | 68% |
| 13 | 2000 | 61% | 88% | 75% |

EXAMPLE 6

This example compares reactions with and without ammonium phosphate catalyst.

In a manner similar to Example 2, 1:1 mixtures of nylons 6,6 and 6 were reacted with ammonia at 320° C. at 1000 psig and an ammonia flow rate of 2.0 mL/min (liquid ammonia) without and with the presence of $(NH_4)_2HPO_4$ (0.25 g) for 30 minutes. The results are compared in Table 4.

TABLE 4

Effect of Catalyst

| Item | Catalyst $(NH_4)_2HPO_4$ | Monomeric Products from 66 | Monomeric Products from 6 | Overall Yield to Monomeric Products |
|---|---|---|---|---|
| 14 | no | 10% | 22% | 16% |
| 15 | yes | 19% | 41% | 30% |

EXAMPLE 7

In a manner similar to Example 2, nylon 6,6 (7.5 g), nylon 6 (7.5 g), and $(NH_4)_2HPO_4$ (0.50 g) were reacted with ammonia at 330° C. and 2000 psig (liquid ammonia flow rate of 3.0 mL/minute) for 90 minutes. Product yields (mole percent based on nylon charged) were: HMD, 72%; ADN, 52%; CVAM, 5%; CL, 27%; 6ACN, 70%; ACAM, 1%. This provides an overall yield to monomeric products of 81%.

Examples 8-10 illustrate the less preferred batch method.

EXAMPLE 8

A stainless steel pressure vessel (about 125 mL volume) was charged with nylon 6,6 (30.0 g), $(NH_4)_2HPO_4$ (1.0 g) in the absence of air. The sealed vessel was heated to 150° C., pressurized with ammonia to 2000 psig, then heated to 300° C. and repressurized to 5000 psig. Heating at 300° C. was continued while shaking for 1 hour. Upon cooling and venting, a beige solution was recovered which upon analysis by gas/liquid chromatography revealed the presence of HMD, 12%; ADN, 2%; CVAM, 8%; where the product mole percent observed is based on the equivalents of nylon 6,6 charged. Overall yield to monomeric products is 11%.

EXAMPLE 9

In a manner similar to Example 8, nylon 6,6 (30.0 g) and $BPO_4$ (1.0 g) were heated at 300° C. and 5000 psig ammonia for 1 hour. Product yields were HMD, 16%; ADN, 4% and CVAM, 9%. Overall yield to monomeric products is 15%.

EXAMPLE 10

In a manner similar to Example 8, a stainless steel pressure vessel (about 25 mL volume) was charged with nylon 6,6 (1.00 g), nylon 6 (1.00 g), and $(NH_4)_2HPO_4$ (0.20 g) and heated at 300° C. and 3950 psig ammonia for 6 hours. Product yields (mole percent based on nylon charged) were: HMD, 52%; ADN, 15%; CVAM, 25%; CL, 45%; 6ACN, 45%; ACAM, 8%. Overall yield to monomeric products is 72%.

I claim:

1. A process for preparing a mixture of hexamethylene diamine, adiponitrile and 5-cyanovaleramide consisting of reacting polyhexamethylene adipamide with at least 1 equivalent of ammonia per amide group of the polymer, optionally in the presence of a phosphate catalyst, at a temperature between 250° C. and 400° C. and at a pressure of at least 100 psig.

2. A process according to claim 1 wherein the reaction is carried out in the presence of a phosphate catalyst.

3. A process according to claim 1 wherein the reaction is carried out at a temperature between 300° and 350° C.

4. A process according to claim 1 wherein the reaction is carried out at a pressure between 500 and 2500 psig.

5. A process according to claim 2 wherein the phosphate catalyst is selected from the group of phosphoric acid, an ammonium phosphate or $BPO_4$.

6. A process for preparing a mixture of monomers suitable for conversion to hexamethylenediamine comprising reacting a mixture of polyhexamethylene adipamide (nylon 6,6) and polycaproamide (nylon 6) with at least 1 equivalent of ammonia per amide group of the polymers at a temperature between 250° and 400° C. and at a pressure of at least 100 psig, the ratio of nylon 6,6 to nylon 6 being from 1:9 to 9:1 on a weight basis.

7. A process according to claim 6 wherein the reaction is carried out in the presence of a phosphate catalyst.

8. A process according to claim 6 wherein the reaction is carried out at a temperature between 300° and 350° C.

9. A process according to claim 6 wherein the reaction is carried out at a pressure between 500 and 2500 psig.

10. A process according to claim 7 wherein the phosphate catalyst is selected from the group consisting of phosphoric acid, an ammonium phosphate and $BPO_4$.

* * * * *